US00PP14274P29

(12) United States Plant Patent
Meilland

(10) Patent No.: US PP14,274 P2
(45) Date of Patent: Nov. 4, 2003

(54) MINIATURE ROSE PLANT NAMED 'MEISKAILLE'

(50) Latin Name: *Rosa hybrida*
Varietal Denomination: Meiskaille

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 10/353,916

(22) Filed: Jan. 30, 2003

(51) Int. Cl.[7] ..... A01H 5/00
(52) U.S. Cl. ..... Plt./118
(58) Field of Search ..... Plt./118, 117, 116, Plt./119

*Primary Examiner*—Bruce R. Campell
*Assistant Examiner*—Annette H. Para
(74) *Attorney, Agent, or Firm*—Burns, Doane, Swecker & Mathis, L.L.P.

(57) ABSTRACT

A new and distinct variety of rose plant of the Miniature Class is provided which abundantly forms in clusters on a nearly continuous basis attractive very double bright Lemon Yellow blossoms that well retain their coloration upon maturity. The growth habit is narrow bushy. Very dense dark green semi-glossy foliage is formed that contrasts nicely with the blossom coloration. Plants of the new variety develop well following budding and following the rooting of cuttings. The new variety is well suited for pot forcing under greenhouse growing conditions to form a distinctive gift plant. Very good tolerance to Oidium Botrytis is displayed.

1 Drawing Sheet

Figures 1, 2, 3, 4, 5, 6, 7, 8, 9, 10, 11, 12, 13, 14, 15, 16:
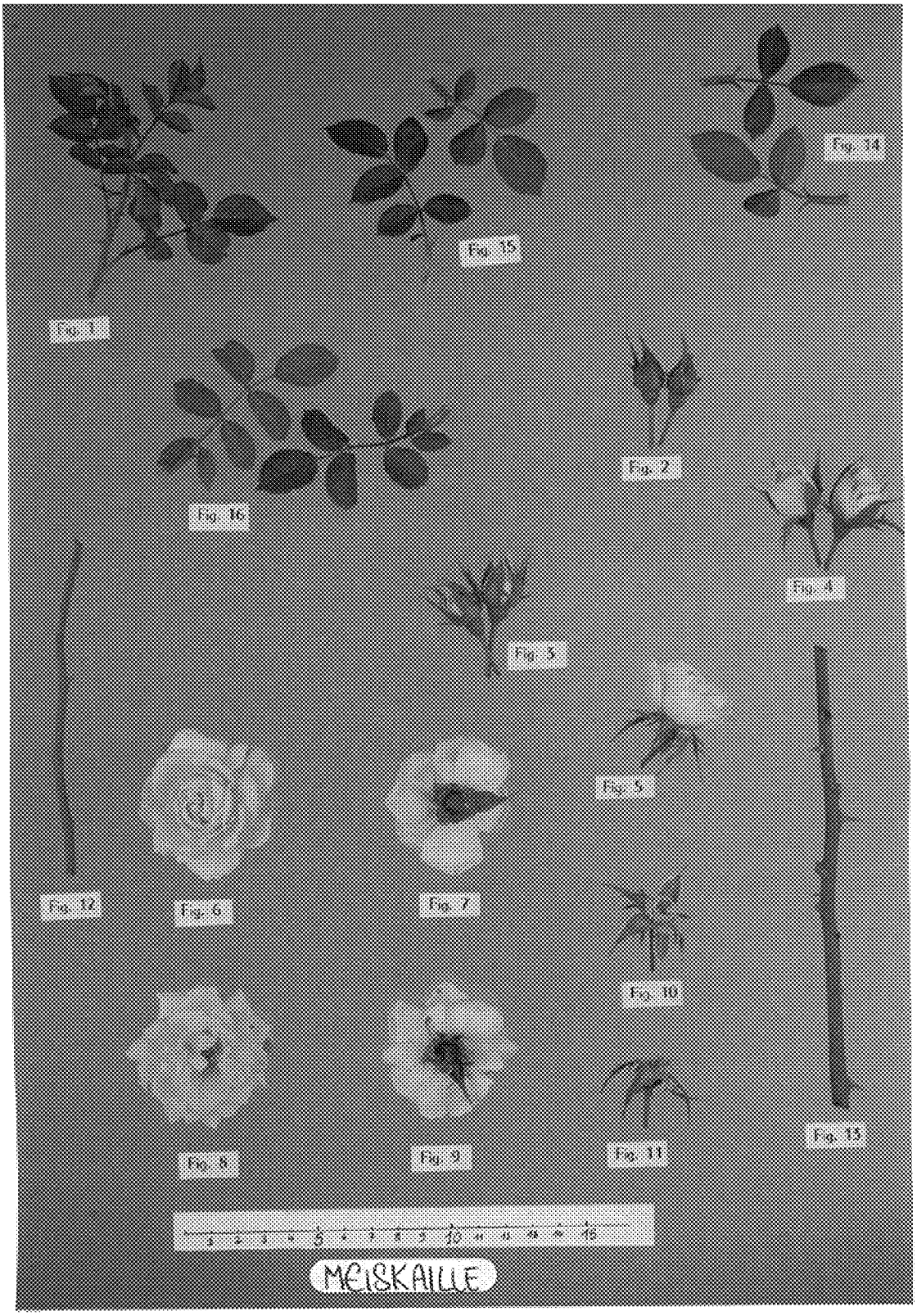

Botanical/commercial classification: *Rosa hybrida*/ Miniature Rose Plant.
Varietal denomination: cv. 'Meiskaille'.

SUMMARY OF THE INVENTION

The new variety of *Rosa hybrida*Miniature rose plant was created by artificial pollination wherein two parents were crossed which previously had been studied in the hope that they would contribute the desired characteristics. The female parent (i.e., the seed parent) of the new variety was the product of the cross of the 'Meineyta' variety (non-patented in the United States) and an unnamed seedling (non-patented in the United States). The 'Meineyta' variety is marketed under the CUMBA MEILLANDIA trademark. The male parent (i.e., the pollen parent) was the 'Savagood' variety (U.S. Plant Pat. No. 7,761). The parentage of the new variety can be summarized as follows:

('Meineyta'×Unnamed Seedling)×'Savagood'.

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) exhibits a narrow bushy growth habit, (b) forms in abundance in clusters on a nearly continuous basis attractive very double bright Lemon Yellow blossoms that well retain their coloration upon maturity, (c) forms very dense dark green semi-glossy foliage, (d) develops well following budding and following the rooting of cuttings, and (e) is well suited for pot forcing under greenhouse growing conditions.

The new variety well meets the needs of the horticultural industry. It is particularly well suited for pot forcing under greenhouse growing conditions to form a distinctive gift plant.

The new variety can be readily distinguished from its parental varieties. More specifically, the 'Meineyta' variety forms bicolored orange-yellow blossoms and a more divergent growth habit. The 'Savagood' variety displays small medium yellow urn-shaped blossoms.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another. Good plant development is displayed regardless of the mode of asexual propagation.

The new variety has been named the 'Meiskaille' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during June while growing on their own roots in greenhouses at Le Cannet des Maures, Var, France. Dimensions in centimeters are shown at the bottom of the photograph.

FIG. 1—illustrates a specimen of a young shoot;

FIG. 2—illustrates specimens of two floral buds before the opening of the sepals;

FIG. 3—illustrates specimens of two floral buds at the opening of the sepals;

FIG. 4—illustrates specimens of two floral buds at the opening of the petals;

FIG. 5—illustrates a specimen of a flower during the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets—plan view—upper surface (top), and—under surface (bottom);

FIG. 15—illustrates specimens of leaves with five leaflets—plan view—under surface (right), and—upper surface (left); and FIG. 16—illustrates specimens of leaves with seven leaflets—plan view—upper surface (right), and—under surface (left).

DETAILED DESCRIPTION

The chart used in the identification of the colors is that of The Royal Horticultural Society (R.H.S. Colour Chart). The description is based on the observation of one year-old specimens of the new variety which were observed during June while growing on their own roots in greenhouses at Le Cannet des Maures, Var, France.

Class: Miniature.

Plant:

*Height.*—Approximately 30 to 35 cm on average at the end of the growing season.

*Width.*—Approximately 35 to 40 cm on average at the end of the growing season.

*Habit.*—Narrow bushy.

Branches:

*Color.*—Young stems: near Yellow-Green Group 146C. Adult wood: near Yellow-Green Group 146B.

*Thorns.*—Size: commonly in excess of 5 mm. Quantity: approximately 9 on average on a stem length of 20 cm. Color: near Yellow-Green Group 152D on adult stems. Configuration: rather straight and elongated on the upper surface and slightly concave on the under surface.

Leaves:

*Petioles.*—Upper surface: smooth, and near Green Group 137B and lightly suffused with Greyed-Red Group 178A in coloration. Under surface: commonly possess a few tiny prickles and near Green Group 147C in coloration.

*Stipules.*—Adnate, pectinate, and approximately 1.2 cm in size on average.

*Leaflets.*—Number: 3, 5 (most often), and 7. Shape: generally elliptic with a symmetrical tip and a rounded base (as illustrated). Texture: consistent. Serration: simple and regular. General appearance: very dense, dark green, and semi-glossy. Size: approximately 2.5 cm in length on average, and approximately 1.8 cm in width on average for the terminal leaflet. Color (young foliage): Upper surface: near Yellow-Green Group 146A and edged with Greyed-Red Group 178C. Under surface: near Yellow-Green Group 146A and edged with Greyed-Red Group 178C. Color (adult foliage): upper surface: near Green Group 137A. Under surface: near Yellow-Green Group 147B.

Inflorescence:

*Number of flowers.*—Commonly in a flat cluster of approximately 2 to 5 per stem.

*Peduncle.*—Near Yellow-Green Group 146C in coloration, glandular, and the length commonly is approximately 6 cm on average.

*Sepals.*—Upper surface: tomentose and near Yellow-Green Group 147C in coloration. Under surface: glandular and near Yellow-Green Group 146A and 146B in coloration. Shape: with a few foliaceous extensions (as illustrated).

*Buds.*—Shape: ovoid. Size: medium for class, and approximately 1 to 1.5 cm in length. Color: as the calyx breaks near Yellow Group 13A on the upper surface and the under surface. Basal petal spot: none observed.

*Flower.*—Form: very double, and cup-shaped. Diameter: approximately 6 cm on average when fully open. Color (when blooming): upper surface: bright Lemon Yellow, near Yellow Group 13A. Under surface: bright Lemon Yellow, near Yellow Group 13A. Basal petal spot: none observed. Stability of coloration: very good with coloration commonly being well maintained upon full maturity. Fragrance: none. Anthers: regularly arranged around the styles, near Yellow-Orange Group 22A in coloration, and approximately 0.2 cm in size. Pollen: near Yellow-Orange Group 14A in coloration. Stamen number: approximately 141 on average. Filaments: near Yellow-Orange Group 22B in coloration, and approximately 0.5 cm in length on average. Pistil number: approximately 96 on average. Petal configuration: wedge-shaped base, with an acuminate tip, and edges that are undulated and reflexed. Petal number: approximately 44 to 46 on average under normal growing conditions. Petal texture: strong. Petal arrangement: imbricated. Petal drop: good, the petals commonly detach cleanly before drying. Stigmas: near Yellow-Orange Group 19C in coloration. Styles: near Yellow Group 2D in coloration, and approximately 1 cm in length on average. Stigma: near Yellow Group 2D in coloration, and approximately 0.1 cm in size on average. Receptacle: smooth, near Yellow-Green Group 146A in coloration, pitcher-shaped in longitudinal section, approximately 0.9 cm in length on average, and approximately 1 cm in width on average. Hips: near Yellow-Orange Group 23B in coloration. Seeds: commonly approximately 12 per hip, and near Yellow-Orange Group 18D in coloration. Lasting quality: very long on the plant with the blossoms commonly lasting approximately 10 to 12 days on average.

Development:

*Vegetation.*—Strong.

*Blooming.*—Very abundant and nearly continuous.

*Resistance to diseases.*—Very good tolerance to Oidium Botrytis, and slight sensitivity to Black Spot.

*Aptitude to bear fruit.*—Good.

I claim:

1. A new and distinct variety of Miniature rose plant characterized by the following combination of characteristics:

(a) exhibits a narrow bushy growth habit, (b) forms in abundance in clusters on a nearly continuous basis attractive very double bright Lemon Yellow blossoms that well retain their coloration upon maturity, (c) forms very dense dark green semi-glossy foliage, (d) develops well following budding and following the rooting of cuttings, and (e) is well suited for pot forcing under greenhouse growing conditions;

substantially as herein shown and described.

* * * * *

McISKAILLE

UNITED STATES PATENT AND TRADEMARK OFFICE

CERTIFICATE OF CORRECTION

PATENT NO. : PP 14,274 P2
DATED : November 4, 2003
INVENTOR(S) : Alain A. Meilland It is certified that error appears in the above-identified patent and that said Letters Patent is hereby corrected as shown below:

Title page,
Insert Item

-- [65] Prior Publication Data

EP 2002/0848 June 10, 2002 --.

Signed and Sealed this

Fourth Day of May, 2004

JON W. DUDAS
*Acting Director of the United States Patent and Trademark Office*